(12) United States Patent
Ghahremani

(10) Patent No.: US 11,717,184 B2
(45) Date of Patent: Aug. 8, 2023

(54) TRACKING HEAD MOTION FOR MEDICAL IMAGING

(71) Applicant: Siemens Medical Solutions USA, Inc., Malvern, PA (US)

(72) Inventor: Ahmadreza Ghahremani, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 466 days.

(21) Appl. No.: 16/592,063

(22) Filed: Oct. 3, 2019

(65) Prior Publication Data

US 2020/0214589 A1 Jul. 9, 2020

Related U.S. Application Data

(60) Provisional application No. 62/788,974, filed on Jan. 7, 2019.

(51) Int. Cl.
| | | |
|---|---|---|
| A61B 5/00 | (2006.01) | |
| A61B 5/055 | (2006.01) | |
| A61B 6/03 | (2006.01) | |
| A61B 5/11 | (2006.01) | |
| A61B 6/04 | (2006.01) | |
| A61B 6/00 | (2006.01) | |
| G06T 7/00 | (2017.01) | |

(52) U.S. Cl.
CPC ............. *A61B 5/055* (2013.01); *A61B 5/11* (2013.01); *A61B 5/7207* (2013.01); *A61B 6/037* (2013.01); *A61B 6/04* (2013.01); *A61B 6/5264* (2013.01); *A61B 6/547* (2013.01); *G06T 7/0012* (2013.01)

(58) Field of Classification Search
CPC ........ A61B 5/055; A61B 5/11; A61B 5/7207; A61B 6/037; A61B 6/04; A61B 6/5264; A61B 6/547; A61B 6/032; A61B 6/501; G06T 7/0012
See application file for complete search history.

(56) References Cited

U.S. PATENT DOCUMENTS

| | | | |
|---|---|---|---|
| 2017/0173262 A1* | 6/2017 | Veltz | G16H 20/17 |
| 2018/0350081 A1* | 12/2018 | Hsieh | A61B 5/0064 |
| 2019/0000318 A1* | 1/2019 | Caluser | A61B 5/0073 |
| 2019/0182415 A1* | 6/2019 | Sivan | G06F 3/012 |

* cited by examiner

*Primary Examiner* — Joel Lamprecht

(57) ABSTRACT

Systems and methods for tracking head motion during medical imaging. In accordance to one aspect, a head holder for a medical scanner is provided. The head holder includes at least one movable component that moves with patient's head while the head is placed on the movable component during brain imaging. The head holder further includes one or more inertial measurement units (IMUs) attached to the movable component that measure motion data, wherein any change in orientation of the movable component indicated by the motion data represents movement of the head. The one or more IMUs may communicate with a computer system during brain imaging in substantially real time to record motion parameters.

19 Claims, 4 Drawing Sheets

TRACKING HEAD MOTION FOR MEDICAL IMAGING

CROSS REFERENCE TO RELATED APPLICATIONS

This application claims priority to U.S. Provisional Application Ser. No. 62/788,974 filed on Jan. 7, 2019, the contents of which are incorporated by reference.

TECHNICAL FIELD

The present disclosure generally relates to tracking head motion for medical imaging.

BACKGROUND

Medical imaging techniques, such as positron emission tomography (PET), are used to obtain images of the interior of a patient's body for long scan time duration. During this procedure, if any movement occurs, it will create blurring artifacts in the reconstructed image. To create a high-resolution static image, many events need to be acquired from detectors inside the scanner for a long scan time. This phenomenon is more critical for brain images because image quality needs to be good enough to be analyzed by a physician.

In nuclear imaging modalities, especially in hybrid medical scanners such as a combination of single photon emission computed tomography and computed tomography (SPECT/CT), a combination of positron emission tomography and computed tomography (PET/CT), performing a series of image acquisitions can take a considerable amount of time. In the hybrid version of scanners, the PET scanner needs to use image data captured previously from the CT scanner e.g., to estimate correct attenuation map which is very useful for accurate reconstruction of PET images. Precise matching between both scanners is crucial.

In hybrid medical scanners, the reconstructed image is from a combination of acquiring data within the short scan (CT scan) and long scan (PET scan). Any patient movement during this process may cause blurring or other artifacts that reduce image quality or usability. Also, for special medical treatment like radiotherapy, tracking the position of a patient's head for a certain region during scan or treatment is important. However, it is frequently difficult for patients to remain still without any movement during the entire data acquisition process or portions thereof. For example, one form of motion frequently encountered in image acquisition is head motion during a PET scan of the brain. In hybrid scanners, CT data is used for attenuation correction of such images. However, head motion results in mismatches between CT and the PET emission data, which leads to reduced image quality. Lack of a correct attenuation map based on the new positions of the head during PET scan can cause blurring of images, since wrong attenuation map is used for reconstruction.

Traditional methods to prevent or minimize patient movement are either uncomfortable or fail to adequately manage the patient movement. Presently known methods of tracking and monitoring the patient movement, such as techniques based on depth camera (e.g., time-of-flight (TOF) cameras or structured light camera), generally require complex hardware and software algorithms and fail to provide accuracy, reliability, simplicity, user friendliness and low interference with PET/CT or SPECT/CT environment.

SUMMARY

Described herein are systems and methods for tracking head motion during medical imaging. In accordance to one aspect, a head holder for a medical scanner is provided. The head holder includes at least one movable component that moves with the head of the patient during brain imaging. One or more inertial measurement units (IMUs) are attached to the movable component to measure motion data, wherein any change in orientation of the movable component indicated by the motion data represents movement of the head. The one or more IMUs may communicate with a computer system during brain imaging in substantially real time to record motion parameters.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1A:
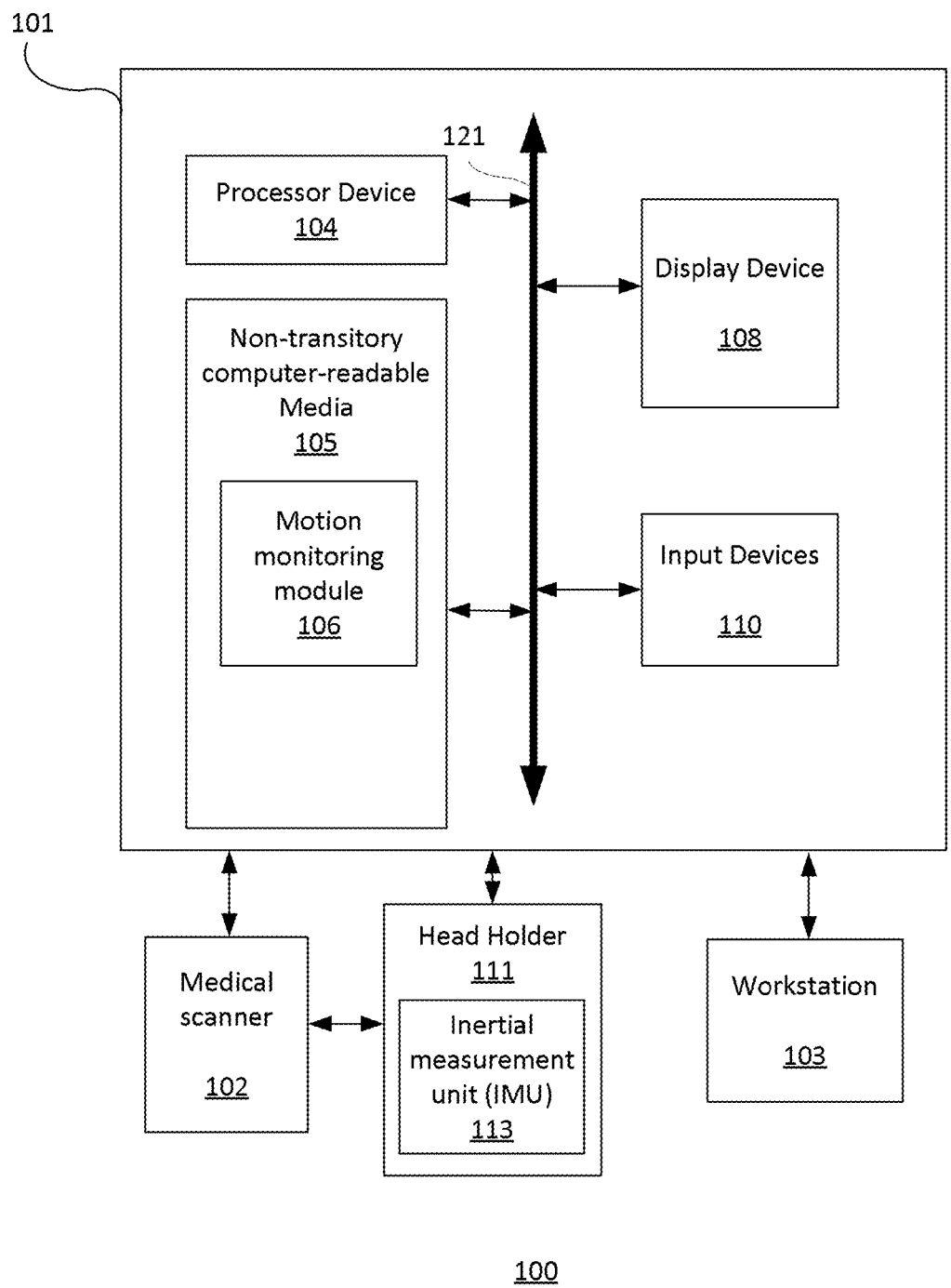
FIG. 1a is a block diagram illustrating an exemplary hybrid medical imaging system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

One aspect of the present framework provides a head holder equipped with an inertial measurement unit (IMU) to track motion of a patient's head during brain imaging. More particularly, at least one movable component of the head holder moves with the patient's head in many degrees of freedom very loosely (i.e., with minimum friction) during brain imaging (e.g., PET or CT scan). Even very small head motion may be picked up by the IMU attached to the movable component of the head holder. The IMU may communicate with a central computer system in substantially real-time to record current position or motion parameters in time domain (with reasonable sampling rate) during brain imaging.

Simplicity, user-friendly, accuracy, reliability, low cost and very low interference with medical imaging environment provide great advantageous opportunity to acquire very useful datasets regarding head motion. There may be many ways to apply the motion data to perform image reconstruction, since new attenuation maps may be generated based on the motion data. For hybrid scanners (e.g., PET/CT), tracking a patient's head during imaging is very helpful to fix any mismatch between the attenuation map created by CT image data and current PET image data. The IMU device or head holder may be smart enough to communicate with the control unit of the medical scanner to avoid capturing any inaccurate events while large motion occurs (e.g., head motion exceeds certain limits or thresholds like angle). It is understood that while an application directed to tracking head motion in a PET/CT scanner may be shown herein, the technology is not limited to the specific implementations illustrated.

FIG. 1a is a block diagram illustrating an exemplary hybrid medical imaging system 100. The system 100 includes a central computer system 101 for implementing the framework as described herein. Computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. In some implementations, computer system 101 operates as a stand-alone device. In other implementations, computer system 101 may be connected (e.g., using a network) to other machines or devices, such as medical scanner 102, workstation 103 or head holder 111.

Computer system 101 may include a processor device or central processing unit (CPU) 104 coupled to one or more non-transitory computer-readable media 105 (e.g., computer storage or memory), a display device 108 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by motion monitoring module 106.

The head holder 111 disclosed herein can be readily used with different types of medical scanners 102, such as single-photon emission computed tomography (SPECT) system, positron emission tomography (PET) system, PET/CT system, SPECT/CT system, ultrasound system, or external beam radiotherapy system. The head holder 111 may also be used in similar types of medical scanners 102 where the patient needs to remain still during the medical scanning procedure and being able to detect even a subtle movement (or motion) by the patient's head would be useful.

Head holder 111 serves to track motion of a patient's head during a medical scanning procedure. The head holder 111 moves easily with the patient's head with low friction. In some implementations, one or more inertial measurement units (IMUs) 113 are embedded or attached to a movable component of the head holder 111 to measure motion data. The motion data may indicate, for example, the position, rotation, speed, orientation, displacement and/or acceleration of the patient's head in three-dimensional space over time. The movable component of the head holder is preferably very mechanically loose, and the IMU 113 attached to the movable component is able to pick up very small head motion in many degrees of freedom.

IMU 113 is an electronic device that measures and reports a body's motion data using a combination of one or more accelerometers, gyroscopes and sometimes magnetometers. In some implementations, IMU 113 also includes an embedded processor and non-transitory computer-readable media that handle, among other things, signal sampling, buffering, sensor calibration and sensor fusion processing of the sensed inertial data. In other implementations, the processor 104 may perform these functions. IMU 113 may communicate the motion data to medical scanner 102 and/or the computer system 101 via a wired or wireless link for further processing.

Figure 1B:
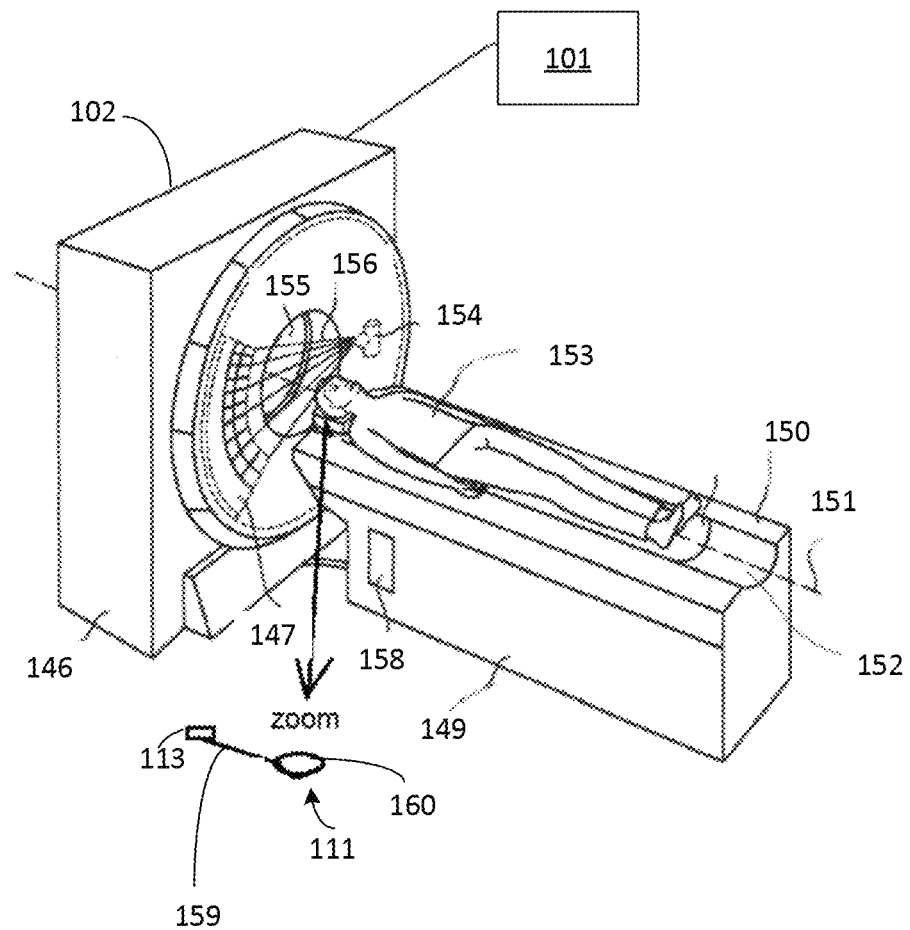
FIG. 1b is a schematic diagram illustrating an exemplary head motion tracking system inside a hybrid scanner.

FIG. 1b is a schematic diagram illustrating an exemplary head motion tracking system 100 inside a hybrid scanner 102 Computer system 101 is communicatively coupled to medical scanner 102. Medical scanner 102 is a hybrid imaging system such as a positron emission tomography (PET)/computed tomography (CT) scanner capable of acquiring both functional (PET) and anatomical (CT) image data. Medical scanner 102 may include a gantry 146, an X-ray detector 147, an X-ray source 154, a PET detector 155 and a control unit 158 for controlling the bed movements. PET detector 155 collects emission data in 3D mode, whereas CT volumes corresponding to the PET field-of-view are obtained during a separate spiral scan by X-ray detector 147 that detects X-rays 156 emitted by X-ray source 154. CT image data has lower statistical noise than PET image data, and it can be used to derive an attenuation map containing attenuation values $\mu$ to correct PET emission data. Use of CT image data reduces the total PET acquisition time and improves precision of attenuation correction factors.

A patient 153 may lie on the surface 152 along a longitudinal axis 151 of a bed 150 that is supported by a table base 149. A head holder 111 is provided to support the patient's head as the patient lies on the bed. The head holder 111 includes an IMU 113, a non-metallic arm 159 and a movable component 160. The head holder 111 tracks any motion of the patient's head during a brain imaging process.

Figure 2:
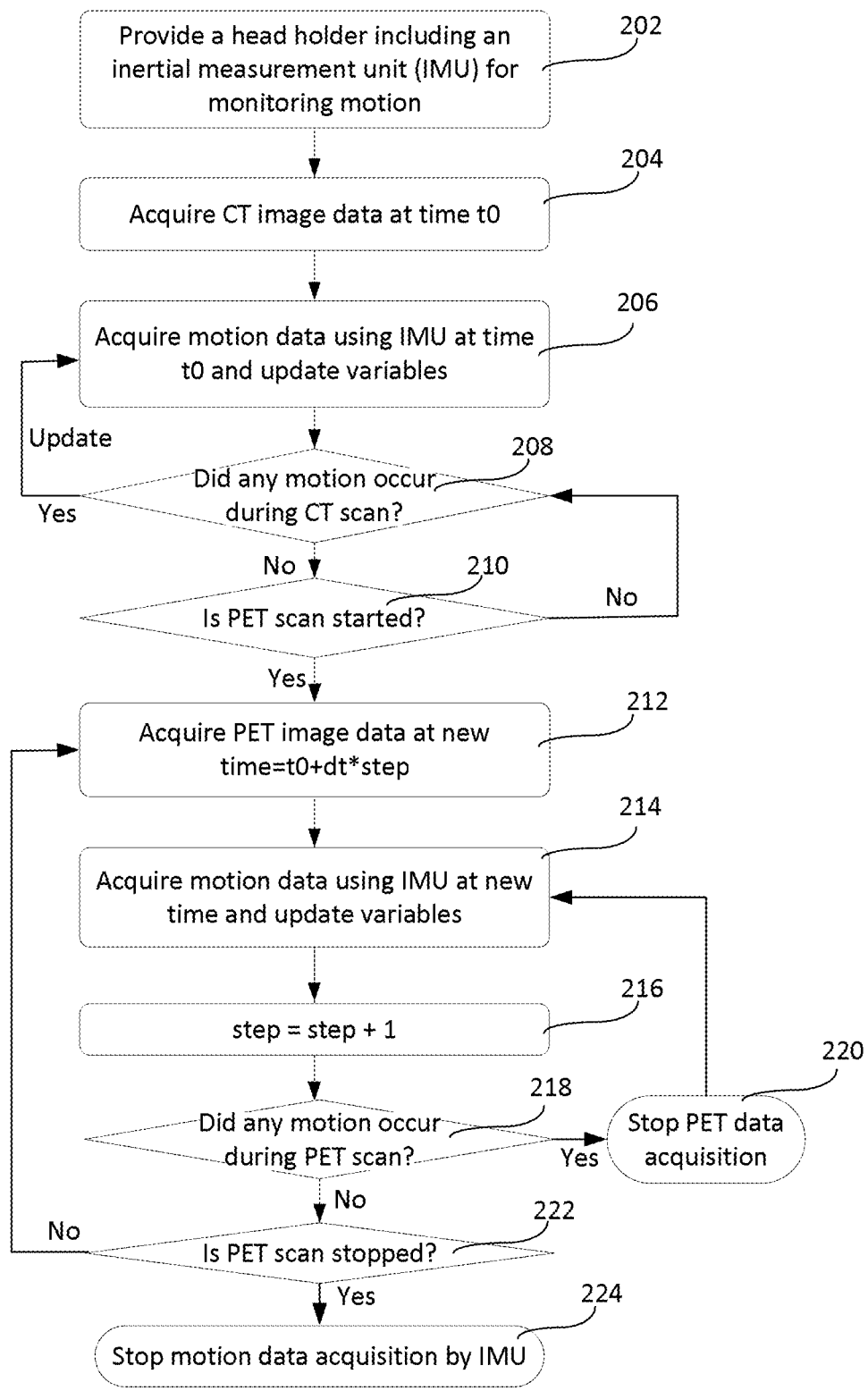
FIG. 2 shows an exemplary image data acquisition method with head motion tracking for a hybrid medical scanner.

FIG. 2 shows an exemplary image data acquisition method 200 with head motion tracking for a hybrid medical scanner. Method 200 may be performed in the order shown or a different order. Additional, different, or fewer steps may also be provided. Further, the method 200 may be implemented with the system 100 of FIGS. 1a and 1b, a different system, or a combination thereof.

At 202, a head holder 111 is provided. The head holder 111 includes at least one movable component that moves easily with minimum friction or with minimum force applied by patient's head while the patient's head is placed on the movable component during imaging of the head. The head holder 111 may be integrated with the patient's bed 150 in the medical scanner 102, or provided as a separate part to be placed on the bed 150 for medical brain imaging. The size of the head holder 111 may be adjustable to be compatible with different head sizes.

At least one inertial measurement unit (IMU) 113 is attached to the movable component to measure motion data in time domain for monitoring movement of the patient's head. The movable component is very mechanically loose, allowing the IMU 113 to pick up very small head motion in three or more degrees of freedom. Any change in position (or orientation) of the movable component indicated by the motion data represents a movement (or motion) by the patient's head. Any variety of motion may be mechanically transferred from the head via the movable part of the head holder to the IMU 113 with minimum force and friction in many degrees of freedom.

The design of the movable component with the attached IMU 113 preferably does not interfere with the imaging procedure and radiation (e.g., gamma rays) used for imaging the patient's head. The IMU 113 may be placed on the movable component with minimum interference with the gamma radiation of the medical scanner. For example, the IMU 113 may be embedded in the movable component and small enough to be located directly under the patient's head. Alternatively, the IMU 113 is placed at an optimized predetermined distance from the patient's head and is out of the field-of-view of the medical scanner.

Figure 3:
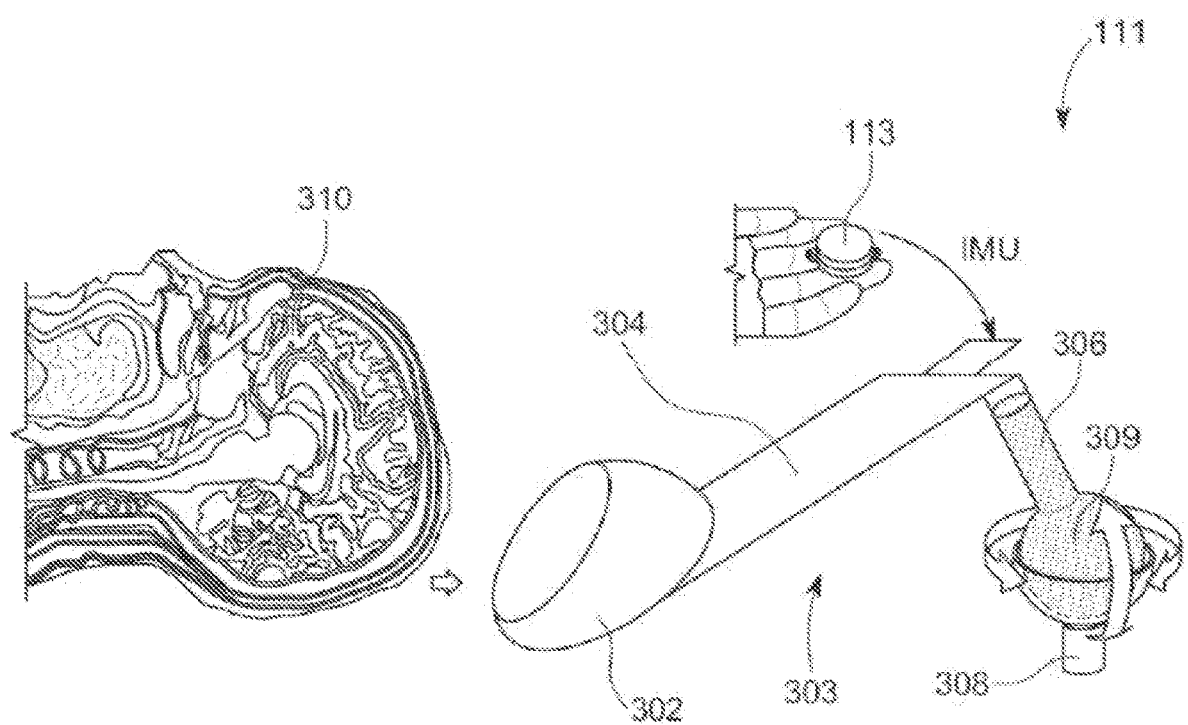
FIG. 3 shows an exemplary head holder.

FIG. 3 shows an exemplary head holder 111. The movable component of the head holder 111 includes non-metallic part 302 which is attached to an articulating arm 303 for supporting a patient's head 310. The non-metallic part 302 and/or the whole structure of the head holder 111 is made from low Z material or with low atomic number to minimize interference with the radiation (e.g., gamma radiation) used for imaging the patient's head. Examples of low Z materials include, but are not limited to, high density polyethylene (HDPE), acrylonitrile butadiene styrene (ABS) and poly (methyl methacrylate) (PMMA), also known as acrylic, acrylic glass or plexiglass. The non-metallic part 302 and the articulating arm 303 move with the patient's head 310 during imaging so that motion can be tracked easily.

The articulating arm 303 is movably connected to a static base member 308 at a joint 309. The joint 309 may be a rotating joint or a ball bearing joint allowing three or more degrees of freedom of rotation with minimum friction and force so that the motion of the patient's head is mechanically transferred to the articulating arm 303. An IMU 113 is attached to the articulating arm 303 for tracking head motion. In some implementations, the articulating arm 303 includes a first support member 304 and a second support member 306. The first support member 304 is a rigid arm that is connected to a second support member 306 at a predetermined fixed angle (e.g., ninety degrees). IMU 113 is positioned at a fixed distance from the non-metallic part 302 along or at an end of the first support member 304 to track head motion. By providing the IMU 113 on the first support member 304, the IMU 113 is advantageously located out of the field-of-view of the medical scanner and does not interfere with the brain imaging process. The second support member 306 is a rigid arm that has a base end that is attached to the static base member 308 at the joint 309.

IMU 113 measures motion data with reasonable sampling rate. IMU 113 may provide submillimeter accuracy in measuring any displacement of the head holder in different orientations. In some implementations, IMU 113 internally uses three different sensing units. These units may be micro-electro-mechanical system (MEMS) sensors that integrate complex mechanical and electronic capabilities on a miniaturized device 113. For orientation determination, the units in IMU device 113 may include a 3-axis gyroscope for detecting angular velocity, a 3-axis accelerometer for detecting direction of the earth's gravity field and a 3-axis magnetometer for measuring direction of the earth's magnetic field. IMU 113 may communicate (e.g., wirelessly) motion data in substantially real time to the medical scanner 102 and/or computer system 101 during brain imaging to record motion parameters in time domain for any online or offline uses.

The articulating arm 303 of head holder 111 moves with minimal friction and is very sensitive to motion. Any movement of the patient's head 310 produces corresponding changes in positions of the articulating arm 303, the non-metallic part 302, and the IMU 113 attached thereto. In other words, head holder 111 preserves head motion precisely, since it moves with minimal force from patient's head in three (or more) degrees of freedom. The head holder 111 mechanically transfers head motion with minimal friction to IMU 113.

Returning to FIG. 2, at 204, hybrid PET/CT imaging system acquires CT image data at an initial time t0.

At 206, IMU 113 acquires motion data (e.g., head holder position) during the CT image data acquisition at initial time t0 as a reference. The motion data is acquired at a reasonable sampling rate. Any change in motion data represents movement (or motion) of the head. In some implementations, IMU 113 records motion data that indicates the position of the head in three-dimensional space over time. The position of the head may be represented by, for example, the position of a normal vector at a reference point (e.g., center point) located on, for example, the head holder 111. Other types of motion data, such as rotation, speed, orientation, displacement and/or acceleration values, may also be recorded. In some implementations, the patient head's position and orientation are described in terms of Euler angles as a set of rotations around a set of X-Y-Z axes of the patient's head. The motion data may be recorded at high precision (e.g., less than 0.01 degrees). IMU 113 precisely measures the displacement in three-dimensional coordinates.

IMU 113 may communicate the motion data to computer system 101 in substantially real-time for updating and/or post-processing. Motion monitoring module 106 may record and/or update motion parameters (e.g., positions) based on the motion data. Initial motion parameters (e.g., initial position of the head holder) at t0 during the CT scan may be set to zero. Normal vectors may be set as a reference. In some implementations, a triggering signal is generated based on the motion data to control the CT image data acquisition.

At 208, motion monitoring module 106 determines if any motion occurred during the CT scan. If the motion of the head exceeds a predetermined threshold value (e.g., more than a predetermined angle), step 206 is repeated to continue acquiring motion data using IMU 113. If the head did not move (or the motion did not exceed a predetermined threshold value), the method 200 proceeds to step 210.

At 210, motion monitoring module 106 determines whether the PET scan is started yet. If the PET scan is not started, step 208 is repeated. If the PET scan is started, the method 200 proceeds to 212.

At 212, hybrid PET/CT imaging system acquires PET image data of the patient's brain (or head) at new time=t0+dt*step, wherein t0 denotes the initial time, dt denotes the time interval and step is an integer that represents a counter number. The counter (step) may be produced by an electronic clock generator and is always running during the PET scan. By multiplying the counter by time interval dt, all events during the PET scan may be recorded in the time domain.

At 214, IMU 113 acquires motion data at the new time during the PET image data acquisition. The motion data is acquired at a reasonable sampling rate. IMU 113 may communicate the motion data to computer system 101 in substantially real-time for updating and/or post-processing. Motion monitoring module 106 records and/or updates motion parameters (e.g., position, rotation) based on the motion data.

At 216, motion monitoring module 106 increases the step to the next step (i.e., step+1).

At 218, motion monitoring module 106 analyzes the motion data to detect any motion of the patient's head occurred during the PET image data acquisition.

If motion is detected, PET image data acquisition is stopped at 220 in the next time step to avoid capturing any inaccurate events while large motion occurs (e.g., head motion exceeds predetermined limits or thresholds such as angle). A triggering signal may be sent to the control unit 158 of the medical scanner 102 to control or stop the PET image data acquisition. In some implementations, the IMU 113 itself is smart enough to stop the PET image data acquisition by communicating with the control unit 158 of the medical scanner 102 to stop the PET image data acquisition.

Steps 214 through 218 are then repeated. If no motion is detected, the method 200 continues to 222.

At 222, motion monitoring module 106 determines if the PET scan is stopped or completed. If not, the method 200 returns to step 212. If PET scan is stopped, method 200 proceeds to 224.

At 224, motion monitoring module 106 stops motion data acquisition by IMU 113.

In some implementations, the motion data may be used for further post-processing. For example, the motion data may be communicated to an image reconstruction module for attenuation correction. The image reconstruction module may generate a new attenuation map based on the new position of patient's head as indicated by the motion data. An image (e.g., PET image) may then be reconstructed based on the new attenuation map. Such attenuation correction may be performed in substantially real time during image data acquisition. The motion data may also be applied to any other motion correction techniques to improve brain image quality.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A head holder for a medical scanner, comprising:
at least one movable component that moves with a head of a patient while the head is placed on the at least one movable component during brain imaging by the medical scanner, and
one or more inertial measurement units attached to the at least one movable component, the one or more inertial measurement units comprising a 3-axis magnetometer for measuring direction of a magnetic field and at least one of a 3-axis gyroscope for detecting angular velocity or a 3-axis accelerometer for detecting direction of a gravitational field, wherein the one or more inertial measurement units measure motion data in the time domain, wherein any change in orientation of the at least one movable component indicated by the motion data represents motion of the head, wherein the one or more inertial measurement units communicate the motion data to a computer system during the brain imaging in substantially real time to record motion parameters.

2. The head holder of claim 1 wherein the medical scanner comprises a hybrid positron emission tomography (PET) and computed tomography (CT) scanner.

3. The head holder of claim 1 wherein the at least one movable component comprises a non-metallic part attached to an articulating arm for supporting the head.

4. The head holder of claim 3 wherein the one or more inertial measurement units are attached to the articulating arm and out of a field-of-view of the medical scanner.

5. The head holder of claim 1 wherein the at least one movable component comprises a non-metallic material with low Z material.

6. The head holder of claim 5 wherein the low Z material comprises high density polyethylene (HDPE), acrylonitrile butadiene styrene (ABS) or poly(methyl methacrylate) (PMMA).

7. The head holder of claim 1 wherein the one or more inertial measurement units are placed at a predetermined distance from the head and out of a field-of-view of the medical scanner.

8. The head holder of claim 1 wherein the one or more inertial measurement units are embedded in the at least one movable component and located directly under the head.

9. A system for head motion tracking, comprising:
a head holder including at least one movable component and one or more inertial measurement units attached to the at least one movable component, the one or more inertial measurement units comprising a 3-axis magnetometer for measuring direction of a magnetic field and at least one of a 3-axis gyroscope for detecting angular velocity or a 3-axis accelerometer for detecting direction of a gravitational field, wherein the at least one movable component moves with a head of a patient while the head is placed on the at least one movable component during brain imaging, wherein the one or more inertial measurement units measure motion data in time domain, wherein any change in the motion data represents motion of the head; and
a computer system communicatively coupled to the one or more inertial measurement units, wherein the one or more inertial measurement units communicate the motion data to the computer system during the brain imaging in substantially real time to record motion parameters.

10. The system of claim 9 wherein the brain imaging is performed by a hybrid scanner.

11. The system of claim 9 wherein the brain imaging is performed by a single-photon emission computed tomography (SPECT) system, a positron emission tomography (PET) system, a SPECT/CT system, a PET/CT system, an ultrasound system or an external beam radiotherapy system.

12. The system of claim 9 wherein the motion data indicates a position, rotation, speed, orientation, displacement or acceleration of the head in three-dimensional space over time.

13. The system of claim 9 wherein the computer system performs motion correction based on the motion data for image reconstruction.

14. The system of claim 9 wherein the head holder is integrated with a bed.

15. The system of claim 9 wherein the head holder is provided as a separate component on a bed.

16. A method for tracking motion of a head comprising:
(i) providing a head holder including at least one movable component and one or more inertial measurement units attached to the at least one movable component, the one or more inertial measurement units comprising a 3-axis magnetometer for measuring direction of a magnetic field and at least one of a 3-axis gyroscope for detecting angular velocity or a 3-axis accelerometer for detecting direction of a gravitational field, wherein the at least one movable component moves with a head of a patient while the head is placed on the at least one movable component;
(ii) acquiring, by the one or more inertial measurement units, a first motion data during computer tomography (CT) image data acquisition of the head;
(iii) acquiring, by the one or more inertial measurement units, a second motion data during position emission tomography (PET) image data acquisition of the head;
(iv) analyzing the second motion data to detect any motion of the head during the PET image data acquisition; and
(v) in response to detecting the motion of the head, stopping the PET image data acquisition.

17. The method of claim 16 further comprises
generating a new attenuation map based on a new position of the head indicated by the second motion data; and
reconstructing a PET image based on the new attenuation map.

18. The method of claim 16 further comprises communicating, by the one or more inertial measurement units, the first and second motion data to a computer system in substantially real time to record motion parameters.

19. The method of claim 16 wherein the in response to detecting the motion of the head, stopping the PET image data acquisition comprises
in response to detecting the motion of the head exceeds a predetermined threshold value, communicating, by the one or more inertial measurement units, with a medical scanner performing the PET image data acquisition.

* * * * *